Figure 2:
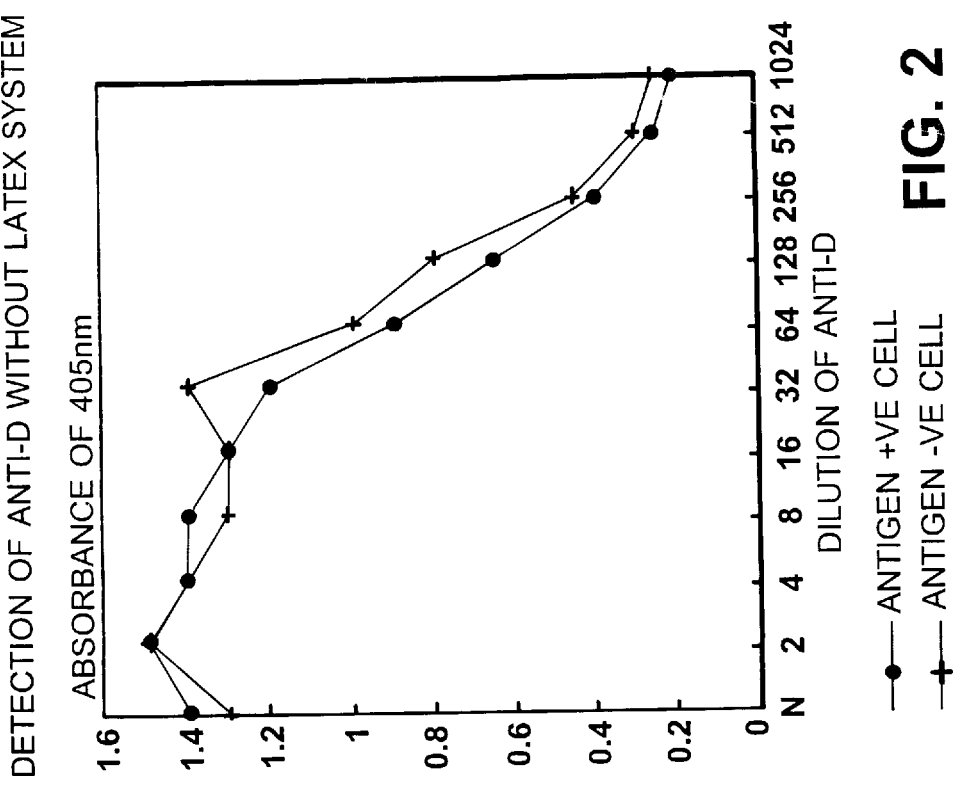

United States Patent [19]

Scott

[11] Patent Number: 5,773,222
[45] Date of Patent: Jun. 30, 1998

[54] SOLID PHASE IMMUNOLOGICAL ASSAY

[75] Inventor: Marion Lesley Scott, Bristol, Great Britain

[73] Assignee: National Blood Authority, Watford, United Kingdom

[21] Appl. No.: 343,580

[22] PCT Filed: May 26, 1993

[86] PCT No.: PCT/GB93/01080

§ 371 Date: Jan. 11, 1995

§ 102(e) Date: Jan. 11, 1995

[87] PCT Pub. No.: WO93/24839

PCT Pub. Date: Dec. 9, 1993

[30] Foreign Application Priority Data

May 27, 1992 [GB] United Kingdom .................. 9211176

[51] Int. Cl.$^6$ ........................ G01N 33/53; G01N 33/567; G01N 33/555; G01N 33/542

[52] U.S. Cl. ........................ 435/7.1; 435/7.2; 435/7.25; 435/7.21; 435/7.9; 435/7.92; 436/518; 436/519; 436/520; 436/521; 436/522; 436/827; 436/828; 436/820; 436/63

[58] Field of Search ........................... 435/7.1, 7.2, 7.25, 435/7.21, 7.9, 7.92; 436/518–522, 827, 828, 820, 63

[56] References Cited

U.S. PATENT DOCUMENTS

| | | |
|---|---|---|
| 3,853,987 | 12/1974 | Dreyer . |
| 4,328,183 | 5/1982 | Rosenfield et al. . |
| 4,452,734 | 6/1984 | Larson et al. . |
| 4,816,413 | 3/1989 | Sinor et al. ............................. 436/520 |
| 5,177,023 | 1/1993 | Sutton et al. ........................... 436/533 |

FOREIGN PATENT DOCUMENTS

| | | |
|---|---|---|
| 0 140 489 | 5/1985 | European Pat. Off. . |
| 0 243 818 | 11/1987 | European Pat. Off. . |
| 0 266 077 | 5/1988 | European Pat. Off. . |
| 0 267 317 | 5/1988 | European Pat. Off. . |
| 0 279 525 | 8/1988 | European Pat. Off. . |
| 0 363 510 | 4/1990 | European Pat. Off. . |
| 0 367 468 | 5/1990 | European Pat. Off. . |
| 0 451 800 | 10/1991 | European Pat. Off. . |
| 0 487 459 | 5/1992 | European Pat. Off. . |
| 2 016 687 | 9/1979 | United Kingdom . |
| 85/01354 | 3/1985 | WIPO . |
| 87/00196 | 1/1987 | WIPO . |
| 88/07680 | 10/1988 | WIPO . |
| 89/06976 | 8/1989 | WIPO . |
| 92/02819 | 2/1992 | WIPO . |
| 9 211 864 | 7/1992 | WIPO . |

OTHER PUBLICATIONS

Webster's II new Riverside Dictionary pp. 1063 and 1116, 1984.

Adair et al, J. Biol. Chem. vol. 249 p. 4649, Aug. 1974.

Iwasa et al., "An Esterase Isozyme in Non. Hemoglobin Proteins of Cell Lysate Reacting with Mushroom Lectin" Tohoku J. Exp. Med., vol. 136:53–59, Jan. 1982.

Kawaguchi et al., "Elucidation of Lectin Receptors by Quantitative Inhibition of Lectin Binding to Human Erythrocytes and Lymphocytes", Biochemistry, vol. 15, No. 21 pp. 4581–1586, 1976.

*Primary Examiner*—Sheela Huff
*Attorney, Agent, or Firm*—Fish & Richardson P.C.

[57] ABSTRACT

A solid phase method of detection or assay of the presence or amount in a serum or plasma sample of a target antibody specific to a cell surface antigen. The sample is contacted with an immobilised preparation of cells bearing the antigen and antibody bound thereto is detected or assayed by means of an indicator comprising a binding partner for the antibody bound to labelled latex particles.

21 Claims, 1 Drawing Sheet

SOLID PHASE IMMUNOLOGICAL ASSAY

BACKGROUND OF THE INVENTION

The present invention relates to a solid phase immunological assay and in particular to a solid phase serological assay for the screening of blood samples.

Immunoassay, and in particular serological assay, is an important and routine aspect of clinical science. The ability to detect blood group specific antibodies in serum of patients prior to transfusion is particularly important. Prior to transfusion, donor and patient blood samples are phenotypically characterised for the major blood group antigens A, B, O, and Rh(D), followed by a further screen for atypical antibodies in the patients' serum such as those with Duffy, Kidd, Kell, MNS and other Rh specificities. Detection and subsequent identification of such irregular antibodies facilitates the selection of appropriate blood for transfusion, i.e. that which does not express antigens against which such irregular antibodies are directed. Transfusion with suitably selected blood avoids transfusion reactions in the patient, which range from a mild febrile reaction to death.

Known serological assays rely on red cell agglutination in liquid suspension for the detection of red cell antigen-antibody interactions. Such tests for antibody detection in patients' sera are essentially manual tests, and are highly subjective, requiring the operator to discriminate visually whether or not agglutination has occurred. Many antibodies which can give rise to clinically significant transfusion reactions if antigen positive blood is transfused in vivo are present at low concentrations and will only promote weak agglutination in vitro, even if undiluted serum/plasma is tested. The performance of such tests in practice shows them to be insensitive and inaccurate, as weak agglutination reactions can easily be missed by less skilled workers.

In other fields solid phase immunoassays are used in which antigen preparations are immobilised on a solid support and exposed to the test sample containing antibodies, whereupon bound antibody is subsequently detected for example by means of an enzyme or radio-labelled secondary antibody. This has the advantage that it is readily adapted to automation and by appropriate choice of a labelling agent, results can be quantitated. Such techniques are highly sensitive.

An application of solid phase techniques to antibody screening for irregular blood cell antibodies has been made using immobilised red cells which are reactive with the target antibody. Such techniques use antiglobulin bound to red cells as a means of detecting an antibody-antigen interaction, by a binding reaction between the antiglobulin and the immobilised target antibody. Such red cells are referred to as 'indicators'. Red cells are prepared for use as indicators either by direct chemical coupling to antiglobulin using, for example, chromic chloride, or by means of an antibody to a red cell antigen, such as anti-Rh (D), which binds both to the red cells and to the antiglobulin reagent. In these systems, a positive reaction is indicated by adhesion of indicator red cells across the solid surface. When the reaction is carried out in a microplate, or other surface provided with recesses, the indicator cells may be centrifuged under appropriate conditions of g force and time onto the surface whereupon in a positive reaction, a monolayer of red cells forms around the well/recess, and in a negative reaction, a button of red cells is formed in the bottom of the well. Reaction is detected by means of visual examination of the indicator red cells, in which case a subjective interpretation of the red cell pattern is required. Automated objective reading of indicator red cell patterns requires image analysis equipment, and the patterns obtained vary with the centrifugation conditions used.

If, however, aqueous labelled, for example enzyme-labelled, secondary antibodies are used as the detection system for antibodies to red cell antigens instead of the indicator red cell labelled secondary antibody, the background signal is unacceptably high. Thus despite the advantages of objective, automated reading such a system would offer, the problem of an unacceptably high background due to detection of non-specifically bound immunoglobulin remains.

Despite the advantages of solid phase techniques, the problem of an unacceptably high background due to non-specific binding remains. Furthermore, it is difficult to provide red cells having uniform properties guaranteed to give constant results in the assay.

SUMMARY OF THE INVENTION

We have now surprisingly found that the background signal can be significantly reduced by using labelled latex particles bearing a binding partner for the target antibody as the detection system.

Thus in one aspect the present invention provides a solid phase method of detection or assay of the presence or amount, in a serum or plasma sample, of a target antibody specific to a cell surface antigen wherein the sample is contacted with an immobilised preparation of cells bearing said antigen and antibody bound thereto is detected or assayed by means of an indicator, said indicator comprising a binding partner for said antibody bound to labelled latex particles.

This technique is particularly suitable for solid-phase antibody screening of blood, particularly human blood, which forms a preferred aspect of the invention. In this case a panel of red cells bearing the antigens corresponding to a number of target antibodies may be used most conveniently immobilised for antibody screening.

The term 'cells' as used herein, unless otherwise stated, includes cell membranes or 'ghosts' which carry the surface antigens of the intact cell but have the advantage of the ability to be stored in dry form.

The immobilizing surface may take any conventional form, for example a plate, tube, stick, bead, particle membrane, filter or gel. However, a surface capable of adaptation for use in an automated system is preferred, particularly a microplate.

The material of which the support is composed may be conventional, for example a plastics material or nitrocellulose, although polystyrene and polyvinyl chloride are preferred.

The antigen preparation may for example, comprise cells, preferably blood cells and more preferably red blood cells, or it may comprise membrane preparations deriving from such cells, for example red cell ghosts (i.e. membranes of lysed red cells).

In the particular application of this technique to pre-transfusion screening of patients' serum for the presence of target antibodies, tests are desirably carried out in parallel in systems using two different immobilised test cells, both cells being group O as confirmed by conventional ABO blood grouping procedures. It is also desirable to exclude cells which express low frequency antigens, i.e. those antigens having a frequency of less than 1 per cent in the general population. The following antigens should desirably be expressed on at least one of the test cells:

C c D E e K k Fy$^a$ Fy$^b$ Jk$^a$ Jk$^b$ S s M N P Le$^a$ and Le$^b$

With appropriate choice of test cells it is possible to use the technique of the present invention not only to screen for irregular antibodies, but to further characterise the specificity of such antibodies by using a wider panel of further test cells of known phenotype.

Suitable screening cells are commercially available, for example from BPL, Elstree, Hertz.

The red cells may be immobilised on the surface in a variety of ways, for example by means of an antibody to a non-blood group antigen expressed on the cell surface or by adhesion using poly-L-lysine, organic dyes or lectins. It is, however, desirable that the reagent used is compatible with the cell surface and able to bind the cells or membranes stably to the surface throughout the assay.

Lectins are preferred, particularly those having a specificity for galactosyl moieties, such as *Agaricus bisporus, Agaricus campestris* or *Bauhinia purpurea* lectin, and this also constitutes a novel aspect of the present invention.

Attachment of red cells to plastic via such lectins has been shown to yield a more uniform robust coating of red cells than methods involving the use of chemicals (poly-L-lysine or organic dyes) or antibodies. This was assessed by visual microscopic examination of microplates coated with red cells under different conditions, and by the strength of reaction given by antibodies at limiting dilution when tested by the entire method. At limiting antibody dilution, the degree of signal obtained is dependent on the number of antigen sites available.

Cells, or ghosts may be allowed to coat the solid support surface simply by contact e.g. by settling under gravity, or coating may be assisted and the speed of coating increased, for example by centrifuging the cells onto the surface. Use of ghosts as opposed to whole cells is preferred since we have found ghosts to be more stable on the solid phase on storage. Ghosts may either be prepared in situ on the solid phase by lysing red cells which have been immobilised on the solid surface, or they may be prepared in suspension and then allowed to settle onto the surface or centrifuged.

A further advantage of using ghosts as the cell preparation is that ghosts can be dried onto plates and preserved. Thus test plates can be prepared in bulk and stored for future use. Ghosts may be dried on plates according to known techniques, for example in the presence of sugars, optionally with protein, under ambient conditions. It is, of course, desirable that the drying technique should not denature the antigens. Such techniques are described in EP-A-140489 and EP-A-367468.

In addition, we have discovered that xylitol, a sugar alcohol with a linear structure, can advantageously be used for the desiccation and storage of red cell membranes. This constitutes a novel aspect of the present invention, and is the preferred method for preserving the red cell membranes during dessication and storage.

The prepared plates may be stored at 4° C., sealed in a light-proof airtight container containing a dessicant pouch.

The test antibody containing solution, for example serum, may be contacted with the immobilised cell membrane and unbound antibody washed off after an appropriate incubation time.

A positive reaction is subsequently detected by means of the indicator reagent. This comprises a suspension of latex particles tQ which a binding partner to the target antibody is bound, the indicator being detectably labelled.

The latex particles may be of diameter 0.8 to 6.4 microns, preferably 2 to 2.4 microns. The latex particles may comprise any suitable material, but polyvinyl toluene is preferred. Non-magnetisable or magnetisable latex may be used. The binding partner may be bound to the particles by any convenient means, for example, passive absorption from solution, followed by washing and blocking of remaining reacting sites in a conventional manner for example with an inert protein such as albumin. The detection system is preferably attached to the particles by preconjugation to the binding partner.

The binding partner for the target antibody may take a variety of forms, and may, for example, comprise an anti-globulin antibody or a fragment thereof, protein A or protein G. Where the antibodies to be detected are human antibodies, the secondary anti-human antibody may be raised polyclonally in species such as rabbits, goats or sheep, or suitable monoclonal antibodies derived from rodent species.

The indicator particles are preferably labelled, for example by any means which permits objective detection, such as an enzyme, e.g. peroxidase, alkaline phosphatase or glucose oxidase; a fluorescent label, for example fluorescein or phycoerythrin; a radioactive label, for example $^{125}$I; or a light emitting molecule, for example luminol. The label used, particularly an enzyme label, should be appropriately chosen according to the type of antigen preparation used in order to avoid spurious results arising from endogenous enzyme within the antigen preparation. Thus since red cells contain peroxidase, peroxidase should not be used as the detectable label when using immobilised whole red cells; alkaline phosphatase provides a suitable alternative. Either may be successfully used for screening with immobilised ghosts. Furthermore, when screening whole red cells, the enzyme chosen may conveniently be one which generates a coloured product for detection distinct from the red colour of the cells. Again, this does not apply if ghosts are used.

The use of an enzyme as a detectable label is advantageous as far as clinical testing is concerned since it enables an antibody screen to be brought into line with other standard ELISA techniques routinely performed in clinical laboratories. In addition, the complete screening technique when carried out using a microplate can be readily adapted for automation using available technology and apparatus, without the need for further specialised equipment or skilled staff expertise. Use of enzyme labels enables the reactions to be objectively assessed by simple spectrophotometric measurement.

For routine testing, the reactants for use in the method of the present invention may be supplied in kit form.

Thus in another aspect, the present invention provides a kit for solid phase detection or assay of the presence or amount in a serum or plasma sample of a target antibody specific to a cell surface antigen, the kit comprising
  a) at least one cell membrane preparation presenting antigens to said antibodies immobilised on a solid support
  b) a detectably labelled indicator reagent comprising a binding partner for said target antibodies bound to latex particles.

Such a kit may also contain appropriate buffers and enzyme substrates and also control sera, both positive and negative.

The invention will now be described by means of the following non-limiting Examples, and drawings.

BRIEF DESCRIPTION OF THE DRAWINGSI

Figure 1:
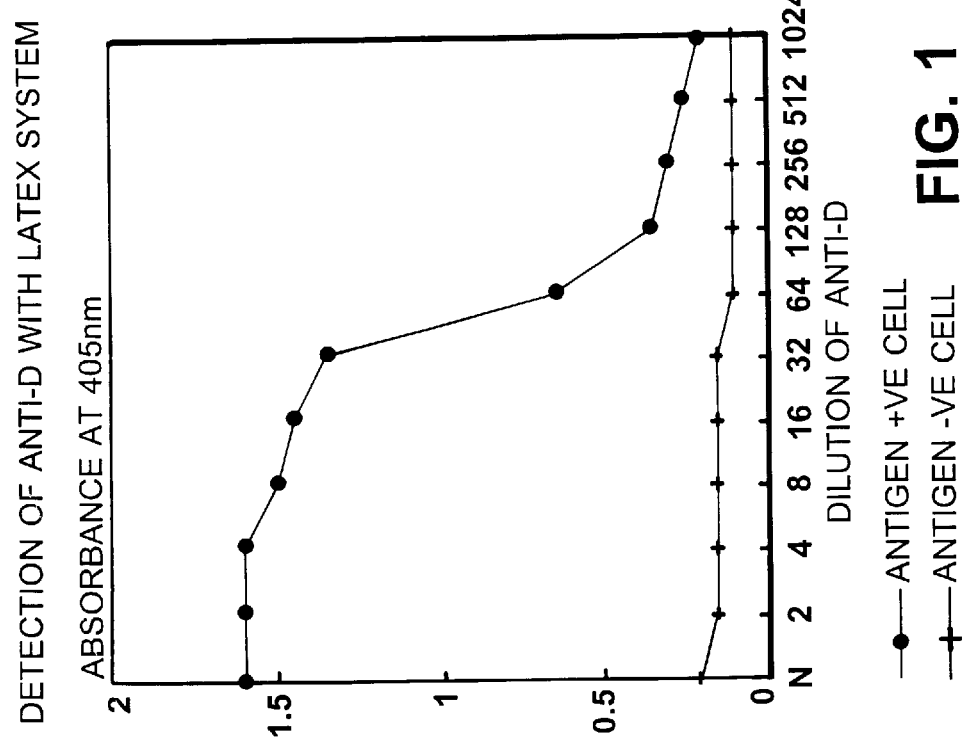

FIG. 1 shows antibody binding to red cells at varying antibody dilutions using the labelled latex system of the invention. In a screening assay, serum containing the antibodies to be detected was contacted with immobilised red blood cells which either express the Rh(D) antigen (—●—) or which do not (—+—). The extent of binding of antibody from the serum sample to the immobilised cells was detected using alkaline phosphatase-conjugated anti-human IgG bound to polyvinyl toluene latex particles.

FIG. 2 shows results obtained from a similar screening assay in which antibody binding was detected using an alkaline phosphatase-conjugated anti-human IgG reagent alone.

Example 1

Immunoassay for the detection of unexpected blood group specific antibodies to human erythrocytes a) Preparation of immobilised red cells A solution of *Agaricus bisporus* lectin (sigma L-5640) was prepared at 10 μg/ml in 20 mM phosphate buffer pH 7.0 containing 1 mM NaCl. 75 μl aliquots were added to the wells of a polystyrene U-well microplate (Sterilin 611U96). The plate was incubated for 1 h at room temperature (18–25° C.). The plate was then washed three times with 10 mM phosphate buffered 0.15M saline pH 7.2 containing 0.055% w/v Tween 20 (PBS/Tween).

Red cells (selected to cover the range of antigens to which antibody detection is desired) were washed three times in PBS and finally suspended to 0.5% in PBS and added to the plates. The microplate was centrifuged for 1 min at 230 g, or the red cells allowed to settle for one hour. The microplate was then washed three times with PBS/Tween to remove excess red cells, leaving a monolayer of red cells around the wells. The integrity of the cell monolayer can be monitored at this stage by microscopic examination. An even monolayer of cells should be visible, with no holes or tears.

If a ghost monolayer is required for assay, the red cells may be then lysed by addition of 5 mM phosphate buffer pH 7.6. The microplate was incubated for 1 min at room temperature with this buffer in the wells, and then the wells were washed twice with the same buffer.

For storage, 75 μl of 1M xylitol solution in 0.15 NaCl was added to the wells, and the microplate incubated for 3 mins at room temperature. Fluid was removed from the wells, and the plate allowed to dry at room temperature for 3 hours. The microplate was then sealed in a suitable air-tight, moisture proof and light proof pouch with a sachet of silica gel dessicant, and stored at 4° C.

b) Preparation of Indicator

The latex detection reagent was prepared by passive adsorption of alkaline phosphatase conjugated anti-human IgG onto 2 μm diameter polyvinyl toluene latex particles. The latex was supplied as a 10% suspension. Latex particles were pelleted by centrifugation, and then resuspended in 5 times the original volume of 20 mM phosphate buffer pH 8.0 containing 1 mM NaCl. The latex was again pelleted. 6/10 of the original volume of an appropriate dilution of alkaline phosphatase labelled anti-human IgG in the same phosphate buffer was added to the latex, and the latex suspended in this solution. This mixture was incubated for 2 hours at room temperature (18–25° C.), then the latex was pelleted and resuspended four times in PBS. The latex was finally resuspended to an appropriate concentration (normally 1/150) in 10 mM tris buffered 0.15M NaCl containing 1 mM $MgCl_2$, 1% bovine serum albumin and 0.1% sodium azide. This detection reagent was stored at 4° C.

c) Screening assay

To use the system for screening a serum/plasma sample for antibodies, a stored microplate was removed from its storage pouch. 50 μl/well of. LISS (low ionic strength solution, 0.24M glycine, 0.03M NaCl, 0.003M phosphate buffer pH 6.7) was added to the wells to be used. 25 μl of the test serum/plasma sample was then added. The microplate was incubated for 15 mins at 37° C., and then washed three times with PBS/Tween. 75 μl/well of latex detection reagent was added, and the microplate centrifuged at 230 g for 1 min, followed by 930 g for 2 mins. Alternatively the latex can be incubated without centrifugation for 1 h at room temperature (18–25° C.). The microplate was then washed four times with PBS/Tween. 75 μl/well of chromogenic enzyme substrate was then added. The substrate solution used for alkaline phosphatase was prepared by dissolving p-nitrophenyl phosphate tablets in 0.1M diethanolamine buffer pH9.8. The microplate was kept at room temperature (18–25° C.) for 15 mins, and the absorbance of the wells read at 405 nm using a through plate spectrophotometer. If the plate cannot be read immediately, the reaction may be stopped by addition of 50 μl/well of 3M NaOH. If plates are stored in the dark at 4° C., the results may be read at any time within the next two days. The absorbance values recorded with the sample were compared to those obtained with positive and negative control sera run in parallel. An absorbance recorded significantly above that of the negative control serum indicates the presence of antibody in the test sample.

The prepared microplates, indicator reagent, LISS solution and alkaline phosphatase substrate tablets and buffer solution may form components of a kit.

Example 2

Comparison of use of latex bound and aqueous enzyme conjugated antiglobulin reagents as detection systems FIG. 1 shows results obtained using the above method with a dilution series of a weak anti-Rh(D) serum tested against $R_1r$ (Rh(D) antigen positive) and rr (Rh(D) antigen negative) red cells. A clear differentiation is shown between the signal recorded with antigen positive and antigen negative red cells. The anti-Rh(D) serum contained 1 IU/ml of anti-D. FIG. 2 shows the results obtained if the same alkaline phosphatase conjugated anti-human IgG reagent is used, but without coupling it to latex. There is no differentiation between the signal recorded with antigen positive and antigen negative cells. These results demonstrate the necessity of using latex in the detection system.

Example 3

Comparison of lectin, poly-L-lysine and Alcian yellow for binding red cells to plastic microplates Different sections of polystyrene and polyvinyl chloride microplates were coated with optimum levels of *Agaricus bisporus* lectin, poly-L-lysine or alcian yellow. (Experiments had previously been conducted to determine the optimum coating concentration of each of these substances). Red cells of phenotypes $R_1 R_1$ (Rh(D) antigen positive) and rr (Rh(D) antigen negative were coated onto the wells as above. Wells were inspected microscopically for integrity of the red cell monolayer. A dilution series of a weak anti-D as above was used according to the method above, using latex bound peroxidase conjugated antiglobulin as the detection system.

The results showed that on both types of microplate the lectin and poly-L-lysine gave rise to complete red cell monolayers with no holes. Several holes were visible in the monolayers on the wells coated with alcian yellow. The absorbances recorded are shown below at 1/64 (a limiting dilution) of the anti-D.

| Plate | "glue" | Absorbance with D +ve | D −ve |
|---|---|---|---|
| PVC | lectin | 1.58 | 0.18 |
| PVC | PLL | 2.00 | 2.00 |
| PVC | Alcian Y | 1.00 | 0.20 |
| PS | lectin | 0.60 | 0.15 |
| PS | PLL | 0.30 | 0.15 |
| PS | Alcian Y | 0.50 | 0.15 |

The results indicate that the jectin overall gives the best performance. Poly-L-lysine gives rise to high backgrounds on PVC plates, and a generally inconsistent performance when duplicates are considered. Alcian yellow gave lower results than the lectin, presumably due to some loss of the ghost monolayer during the assay.

Example 4

Comparison of xylitol, glucose and saline as preservative solutions for dessication of immobilised red cell membranes 1M solutions of xylitol and glucose in 0.15M NaCl and 0.15M NaCl alone were compared as dessicant protective solutions in the above method. (These molarities had previously been shown to be optimal). Antigen positive and antigen negative cells were selected for evaluation with sera containing anti-Rh(D), anti-$Fy^a$, anti-K, anti-S and anti-$Jk^a$. Each serum was tested neat and at a limiting dilution against cells two weeks post-dessication in the various solutions and the same cells that had not been dessicated, but stored as whole blood and freshly immobilised. The results (below) indicate that both glucose and xylitol are suitable dessicant preservatives for the red cell antigens tested.

|  | fresh | xyltl | glcs | NaCl |
|---|---|---|---|---|
| anti-K neat | 1.25 | 1.25 | 1.25 | 0.35 |
| anti-K 1/100 | 1.15 | 1.25 | 0.65 | 0.25 |
| anti-D neat | 0.80 | 1.30 | 1.40 | 0.30 |
| anti-D 1/50 | 0.20 | 0.45 | 0.50 | 0.20 |
| anti-$Fy^a$ neat | 1.20 | 1.50 | 1.40 | 0.30 |
| anti-$Fy^a$ 1/20 | 0.70 | 1.15 | 1.20 | 0.25 |
| anti-$Jk^a$ neat | 1.25 | 1.25 | 1.30 | 0.30 |
| anti-$Jk^a$ 1/20 | 0.45 | 0.65 | 0.85 | 0.25 |
| anti-S neat | 1.30 | 1.50 | 1.20 | 0.40 |
| anti-S 1/20 | 0.45 | 0.80 | 0.70 | 0.35 |

I claim:

1. A solid phase method of detection or assay of the presence or amount, in a serum or plasma sample, of a target antibody specific to a cell surface antigen comprising contacting the sample, suspected containing the target antibody, with an immobilised preparation of cells bearing said antigen and detecting antibody bound thereto by means of an indicator, said indicator comprising a binding partner for said antibody bound to labelled latex particles.

2. The method as claimed in claim 1 wherein the latex particles comprise polyvinyl toluene.

3. The method as claimed in claim 1 wherein the particles are of diameter 0.8 to 6.4 microns.

4. A method as claimed in claim 3 wherein the label on said latex particles is an enzyme.

5. A method as claimed in claim 4 wherein the cells are blood cells.

6. The method as claimed in claim 5 wherein the cells are red blood cells or red blood cell ghosts.

7. The method as claimed in claim 6 wherein the cells are red blood cell ghosts.

8. A method as claimed in claim 7 wherein the cells are immobilized onto a surface by means of a lectin.

9. The method as claimed in claim 8 wherein the lectin has specificity for galactosylmoieties.

10. The method as claimed in claim 9 wherein the lectin comprises *Agaricus bisporus, Agaricus campestris* or *Bauhinia purpurea* lectin.

11. The method as claimed in claim 7 wherein the immobilised ghosts are dried in the presence of a sugar alcohol.

12. The method as claimed in claim 11 wherein the sugar alcohol is xylitol.

13. A kit for solid phase detection or assay of the presence or amount in a serum or plasma sample of a target antibody specific to a cell surface antigen, the kit comprising
   a) at least one cell membrane preparation presenting antigens to said target antibody, said membrane being immobilized on a solid surface; and
   b) a detectably labelled indicator reagent comprising a binding partner for said target antibody bound to latex particles.

14. The method as claimed in claim 3 wherein the cells are blood cells.

15. The method as claimed in claim 14 wherein the cells are red blood cells or red blood cell ghosts.

16. The method as claimed in claim 15 wherein the cells are red blood cell ghosts.

17. The method as claimed in claim 16 wherein the cells are immobilized onto a surface by means of a lectin.

18. The method as claimed in claim 17 wherein the lectin has specificity for galactosyl moieties.

19. The method as claimed in claim 18 wherein the lectin comprises *Agaricus bisporus, Agaricus campestris* or *Bauhinia purpurea* lectin.

20. The method as claimed in claim 19 wherein the immobilized ghosts are dried in the presence of a sugar alcohol.

21. The method as claimed in claim 20 wherein the sugar alcohol is xylitol.

* * * * *